(12) United States Patent
Mourier et al.

(10) Patent No.: US 7,575,930 B2
(45) Date of Patent: Aug. 18, 2009

(54) METHOD FOR ANALYZING OLIGOSACCHARIDES FROM BLOOD PLASMA

(75) Inventors: Pierre Mourier, Charenton le Pont (FR); Christian Viskov, Ris Orangis (FR)

(73) Assignee: Aventis Pharma S.A., Antony (FR)

( * ) Notice: Subject to any disclaimer, the term of this patent is extended or adjusted under 35 U.S.C. 154(b) by 0 days.

(21) Appl. No.: 11/777,431

(22) Filed: Jul. 13, 2007

(65) Prior Publication Data

US 2008/0009069 A1 Jan. 10, 2008

Related U.S. Application Data

(63) Continuation of application No. PCT/FR2006/000112, filed on Jan. 18, 2006.

(30) Foreign Application Priority Data

Jan. 19, 2005 (FR) .................................. 05 00554

(51) Int. Cl.
*G01N 33/00* (2006.01)

(52) U.S. Cl. ........................... 436/94; 436/93; 435/101; 435/105; 435/325

(58) Field of Classification Search ................... 436/94; 435/18, 6; 514/56; 424/63
See application file for complete search history.

(56) References Cited

U.S. PATENT DOCUMENTS

| 5,039,529 | A | * | 8/1991 | Bergendal et al. ............. 424/63 |
| 6,291,439 | B1 | | 9/2001 | Klock |
| 6,617,316 | B1 | * | 9/2003 | Mourier et al. ............... 514/56 |
| 2003/0203385 | A1 | | 10/2003 | Venkatarraman et al. |
| 2004/0265943 | A1 | * | 12/2004 | Viskov et al. ................. 435/18 |
| 2005/0119477 | A1 | | 6/2005 | Mourier |

FOREIGN PATENT DOCUMENTS

WO    WO 00/13027    *    3/2000

* cited by examiner

*Primary Examiner*—Walter D Griffin
*Assistant Examiner*—Christine T Mui
(74) *Attorney, Agent, or Firm*—Ronald G. Ort; James W. Bolcsak

(57) ABSTRACT

The present invention relates to a method for analyzing oligosaccharides constituting the heparins of low molecular weight and the heparins of very low molecular weight from blood plasma.

19 Claims, 2 Drawing Sheets

METHOD FOR ANALYZING OLIGOSACCHARIDES FROM BLOOD PLASMA

A subject matter of the present invention is a method for analyzing oligosaccharides constituting low molecular weight heparins and very low molecular weight heparins from blood plasma.

Heparins are biologically active agents of the glycosaminoglycan family which have particularly useful anti-coagulant properties. Low molecular weight heparins (LMWHs) and very low molecular weight heparins (VLMWHs) are prepared by cutting the long polysaccharide chains of heparin to give shorter chains of low molecular weight.

The oligosaccharides constituting LMWHs and VLMWHs are usually characterized by macroscopic parameters, such as their average molecular weight, or biological activities, such as, for example, the aXa activity (IU/mg). The latter, which measures the interaction with antithrombin III, is the most commonly used.

However, the measurement of these macroscopic parameters or of these biological activities does not allow several crucial questions to be answered. In particular, it is impossible to carry out the analysis of the pharmacokinetic profiles of the various oligosaccharides constituting the LMWHs and VLMWHs on the basis of these criteria. For example, the aXa activity takes into account only the entities with affinity for AT III, that is to say approximately 20% of the mixture only; consequently, the behavior of 80% of the oligosaccharides cannot be measured. Furthermore, the contribution of each entity constituting the affinity mixture cannot be determined.

It is thus impossible to precisely determine the plasma concentration of each oligosaccharide and, with greater reason, its pharmacokinetic profile by simply measuring its aXa activity. In point of fact, these profiles would provide very valuable information for improving the dosage of medicaments based on LMWH and VLMWH.

In order to be able to analyze the behavior of the various oligosaccharides constituting an LMWH or a VLMWH in blood plasma, it is necessary to be able to completely and reproducibly separate these oligosaccharides from the other constituents of the plasma, in particular the proteins. The methods described in the prior art involve strong protease treatments (Volpi et al., 1995, Biochim. Biophys. Acta., 1243 (1), 49-58).

Chromatography or electrophoresis methods make possible analysis of the various constituents of LMWHs. For example, capillary electrophoresis (CE) is used for the separation of heparin oligosaccharides (Guerrini et al., Glycobiology, 2002, 12, 713-719; Linhardt et al., BioMethods, 1997, 9, 183-197). However, the selectivity of CE is fairly low in comparison with liquid chromatography. It is also possible, in some cases, to use MALDI-TOF mass spectrophotometry for the analysis of heparin oligosaccharides but it cannot be applied to complex mixtures, without even mentioning its high cost.

For this reason, analysis of sulfated oligosaccharides, such as those constituting LMWHs and VLMWHs, is carried out in particular by high performance liquid chromatography (HPLC). A method for analysis of LMWHs consisting of an enzymatic depolymerization followed by a reduction, if appropriate, and by HPLC assaying has recently been described (WO 2004/027087). A recent European application (EP04290789.9) discloses a method for the assaying of the oligosaccharides constituting LMWHs and VLMWHs by CTA-SAX anion-exchange chromatography. This method involves anion-exchange chromatography carried out on a quaternary ammonium salt, in particular the cetylmethylammonium, which is absorbed dynamically on a reverse-phase silica column and which maintains a clear and constant positive charge within a pH range of between 2 and 12. This method may involve a preliminary treatment, depolymerization or separation by exclusion chromatography, before the analysis of the LMWHs and VLMWHs by HPLC on the CTA-SAX column.

A subject matter of the present invention is a method for analyzing the oligosaccharides from blood plasma, characterized in that the following two stages are carried out:
treating the sample of blood plasma,
assaying by HPLC.

This method involves neither enzymatic depolymerization nor fractionation by exclusion chromatography of the oligosaccharides present in the sample of blood plasma before assaying by HPLC. On the other hand, according to this method, the sample of blood plasma is treated by filtration so as to separate the oligosaccharides, which are reencountered in the filtrate, from the plasma contaminants, in particular proteins, which remain in the concentrate.

Figure 1:
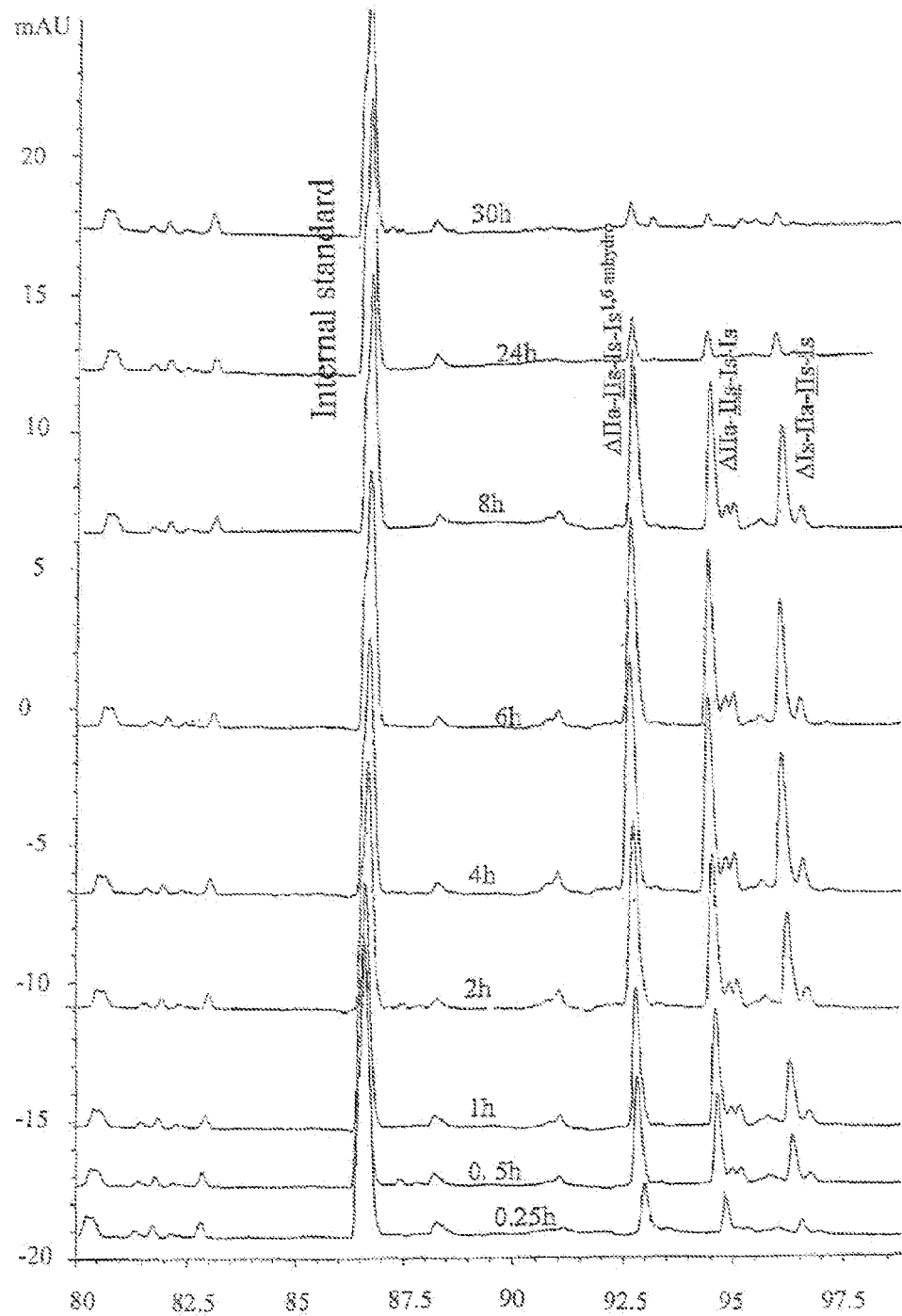
FIG. 1:
Chromatographic monitoring of the pharmacokinetics of 3 octasaccharides for dog 1.

A subject matter of the invention is thus more particularly a method as defined above where the sample of blood plasma is treated by filtration. A very particular subject matter of the invention is a method as defined above, characterized in that the molecules having a molecular weight of greater than 30 kDa are retained in the concentrate.

In order to make possible quantification of the method of treatment of the sample of blood plasma and to verify the reproducibility of this treatment from one sample to another, an internal standard is added, if appropriate, to the sample. This standard has to be an oligosaccharide, if possible structurally close to the assay product, which is mixed with the plasma immediately before filtration.

Another subject matter of the invention is thus a method as defined above, characterized in that a control oligosaccharide is added to the plasma sample immediately before filtration.

Although the majority of the oligosaccharides are separated from the proteins by the filtration, it is possible for a portion to remain trapped by electrostatic interactions with the concentrate. In this case, it is necessary to carry out one or more washing operations on the concentrate in a saline solution.

Another subject matter of the invention is thus a method as defined above and characterized in that the concentrate is washed at least once in a saline solution. According to the invention, the saline solution is preferably a potassium chloride solution.

A subject matter of the invention is more particularly a method as defined above, characterized in that the concentration of the saline solution after addition to the concentrate is greater than or equal to 1M, and very particularly such a method where the saline concentration is greater than or equal to 2M.

After one or more washing operations with a saline solution, the concentrate is washed with water, if appropriate. A subject matter of the invention is thus a method as defined above comprising, after at least one washing operation on the concentrate in a saline solution, a stage of washing with water.

The original filtrate is combined with the filtrates originating from the washing operations and the combined product is diluted 5 times in water. This diluting makes it possible to reconcentrate all the oligosaccharides after the injection on the chromatographic column while preventing any broadening of the peaks caused by an excessively high saline concentration. Immediately before injection, the pH of the solution is adjusted to 3 by addition of 1N HCl.

According to the method according to the invention, the whole of the filtrate and, if appropriate, of the washings is injected directly and analyzed by HPLC.

Anion-exchange HPLC is the separation method best suited to such a complex mixture. In particular, use is made, for the HPLC, of an anion-exchange column with grafting of the quaternary ammonium via a covalent bond. This type of column offers the advantage of being able to use the perchlorate as mobile phase, which is impossible with a CTA-SAX column because of the strong complexing between perchlorate and CTA.

Another subject matter of the invention is thus a method as defined above where the oligosaccharides are assayed by anion-exchange HPLC. A more particular subject matter of the invention is a method as defined above where the oligosaccharides are assayed by HPLC on an anion-exchange column with grafting of the quaternary ammonium via a covalent bond.

Columns of IonPAc AS11 type (Dionex), with a particle size of 9-13 µm and a length of 25 cm, can be used. All the diameters of conventional columns, of between 1 mm and 4.6 mm, can be used but columns with a diameter of 2 mm are preferably used. In a more general context, columns with a smaller diameter, for example 1 mm, can be used, requiring in fact a smaller amount of plasma and also making possible an increase in sensitivity of the analysis.

The apparatus used can be a chromatograph making possible the formation of an elution gradient with a UV detector. Use will preferably be made of a detector equipped with an array of diodes which makes it possible to produce UV spectra of the constituents and to record complex signals, resulting from the difference between the absorptions at two different wavelengths and making possible the detection of acetylated oligosaccharides among the compounds of plasma origin. The use of a mobile phase which is transparent up to 200 nm makes it possible to facilitate the differentiation of the constituents.

The mobile phase used here will preferably be a solution of sodium perchlorate but methanesulfonate or phosphate salts can also be used.

A subject matter of the invention is thus a method as defined above, characterized in that use is made of a mobile phase which is transparent up to 200 nm. In particular, a subject matter of the invention is a method as defined above, characterized in that the mobile phase is a solution of sodium perchlorate, of methanesulfonate or of phosphate. A very particular subject matter of the invention is a method as defined above, characterized in that the mobile phase is a sodium perchlorate solution.

The pH recommended for the separation is between 2 and 6.5. Use will preferably be made of a pH in the region of 3. This pH will be obtained by addition of a salt, such as a phosphate, having a better buffering power at pH=3 than that of perchlorates.

Standard conditions for chromatographic separation are given below, by way of example:

Solvent A: $NaH_2PO_4$ 2.5 mM, brought to pH 2.9 by addition of $H_3PO_4$

Solvent B: $NaClO_{4\,b\,1}N$, $NaH_2PO_4$ 2.5 mM, brought to pH 3.0 by addition of $H_3PO_4$ The elution gradient can be as follows:

T=0 min: % B=3; T=40 min: % B=60; T=60 min: % B=80

For a column with a diameter of 2 mm, the flow rate chosen will be, for example, 0.22 ml/min and the column temperature 40° C.

The oligosaccharides present in the filtered plasma samples are detected by UV. As nonacetylated polysaccharides all have, at a given pH, a virtually identical UV spectrum, it is possible to selectively detect the acetylated sugars by taking as signal the difference between the absorptions at two wavelengths chosen in such a way that the absorptivity of the nonacetylated saccharides is cancelled out.

In the case below, 202 nm and 230 nm will be chosen as reference wavelengths and the signal 202-230 nm will be recorded. It is obvious to a person skilled in the art that the choice of the wavelength will depend on the pH of the mobile phase, it being possible for adjustments of a few nm to be necessary in order to be at the optimum of the said conditions. The most suitable detector for this technique is the DAD detector from Agilent Technologies. In this case, a double detection is carried out on each sample, at 234 nm, on the one hand, and, on the other hand, at 202-230 nm. A triple detection can also be carried out, by in addition measuring the absorption of each sample at 280 nm, which makes it possible to confirm that the signal is not contaminated by protein residues.

A subject matter of the present invention is thus a method as defined above, characterized in that the detection method makes it possible to selectively detect acetylated sugars.

Another subject matter of the present invention is a method as defined above, characterized in that the method for the selective detection of acetylated sugars is carried out by taking, as signal, the difference between the absorption at two wavelengths chosen in such a way that the absorptivity of the nonacetylated saccharides is cancelled out.

A subject matter of the present invention is thus very particularly a method as defined above, characterized in that the method for the selective detection of acetylated sugars is carried out by measuring the absorption at 202-230 nm and 234 nm.

A subject matter of the present invention is thus very particularly a method as defined above, characterized in that the method for the selective detection of acetylated sugars is carried out by measuring the absorption at 202-230 nm, 234 nm and 280 nm.

The method defined above makes it possible more particularly to analyze all β-unsaturated oligosaccharides. More particularly, it applies to the oligosaccharides constituting enoxaparin, octaparin, bemiparin and tinzaparin.

EXPERIMENTAL EXAMPLE

Procedure

Treatment of the Plasma

A plasma sample with a volume of between 100 and 1000 µl is withdrawn and, if appropriate, the internal standard is added to the latter.

After homogenization, the resulting solution is introduced into a 30 kD Ultrafree 05 ultrafiltration cartridge (Millipore) rinsed beforehand with 250 µl of water by centrifuging at 10 000 rev/min for 5 minutes. The plasma is introduced into the upper part of the cartridge once or twice, if the amounts to be filtered are greater than 500 μl.

The cartridge is centrifuged at 10 000 rev/min for between 1 and 2 hours and then the filtrate is withdrawn. If appropriate, the second part of the plasma to be filtered is introduced into the upper part of the cartridge and the latter is again centrifuged. The exact amount of plasma introduced will have been weighed. The cartridge is centrifuged until the protein residue in the upper part of the cartridge represents no more than approximately 10% of the initial part.

The filtrate is withdrawn and 210 μl of 3M KCl per ml of plasma filtered are added to the concentrate.

After homogenization, the cartridge is centrifuged at 10 000 rev/min for between 1 and 4 hours. The cartridge is centrifuged until the protein residue in the upper part of the cartridge represents no more than approximately 10% of the initial part.

The second filtrate is withdrawn and 210 μl of 3M KCl per ml of plasma filtered are added a second time to the concentrate.

After homogenization, the cartridge is centrifuged at 10 000 rev/min for between 1 and 4 hours. The cartridge is centrifuged until the protein residue in the upper part of the cartridge represents no more than approximately 10% of the initial part.

The third filtrate is withdrawn and 250 μl of water per ml of plasma filtered are added.

After homogenization, the cartridge is centrifuged at 10 000 rev/min for between 1 and 4 hours. The cartridge is centrifuged until the protein residue in the upper part of the cartridge represents no more than approximately 10% of the initial part.

The filtrates are combined and diluted 5 fold in water, and the whole is injected directly in anion-exchange HPLC. Immediately before injection, the pH of the injected solution is adjusted to 3 by addition of 1N HCl.

HPLC Method

The filtered plasma is analyzed by anion-exchange HPLC.

The columns used are IonPAc As11 columns (Dionex), with a length of 25 cm and an internal diameter of 2 mm. The detector used is a UV spectrophotometer equipped with an array of diodes.

The whole of the pH is injected after adjustment of the pH to 3 by addition of N HCl. The flow rate chosen is 0.22 ml/min; the column temperature is 40° C.

Elution is carried out in gradient mode. The two solutions used are:

Solvent A: $NaH_2PO_4$ 2.5 mM, brought to pH 2.9 by addition of $H_3PO_4$

Solvent B: $NaClO_4$ 1N, $NaH_2PO_4$ 2.5 mM, brought to pH 3.0 by addition of $H_3PO_4$ The elution gradient is as follows:

T=0 min: % B=3; T=40 min: % B=60; T=60 min: % B=80

Example 1

The evolution of a mixture of three octasaccharides in the blood of male dogs of the beagle breed is monitored. These 3 octasaccharides, symbolized ΔIIaIIsIsIs, ΔIsIIaIIsIs and ΔII-aIIsIsIs$^{1,6\text{-}anhydro}$, are the main affinity octasaccharides of the octasaccharide fractions of Lovenox®. They have a high affinity for ATIII and consequently an antithrombotic activity.

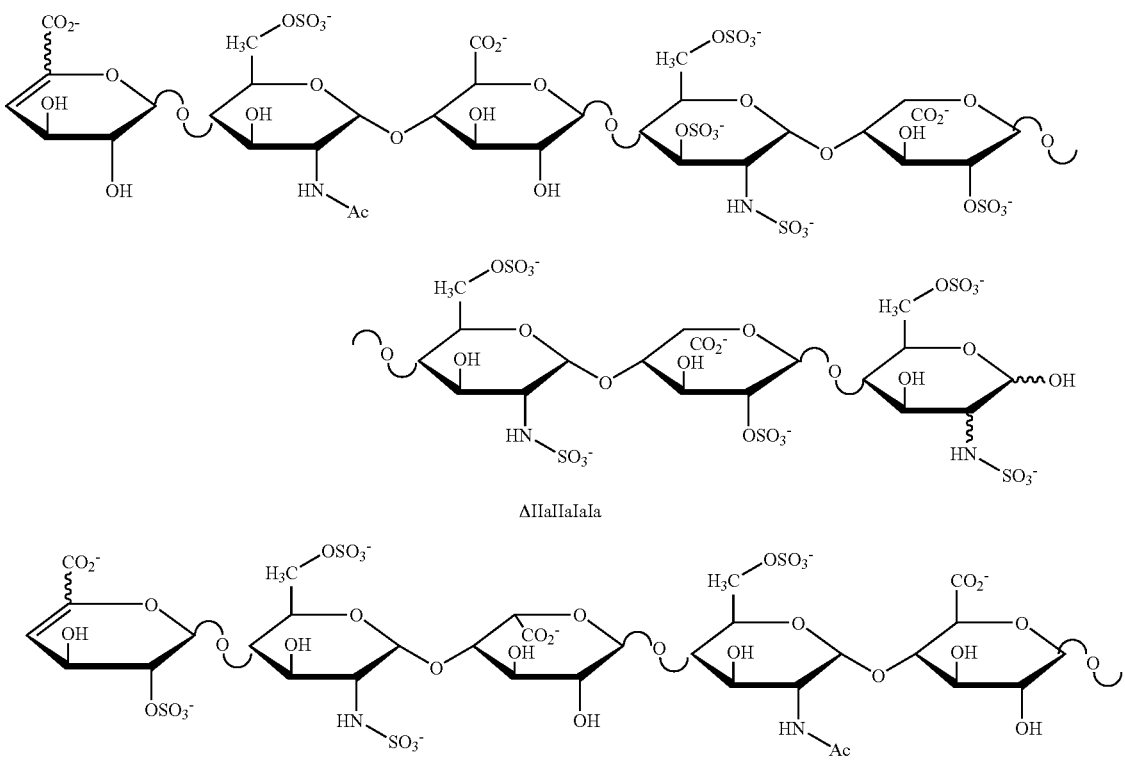

ΔIIaIIaIaIa

-continued

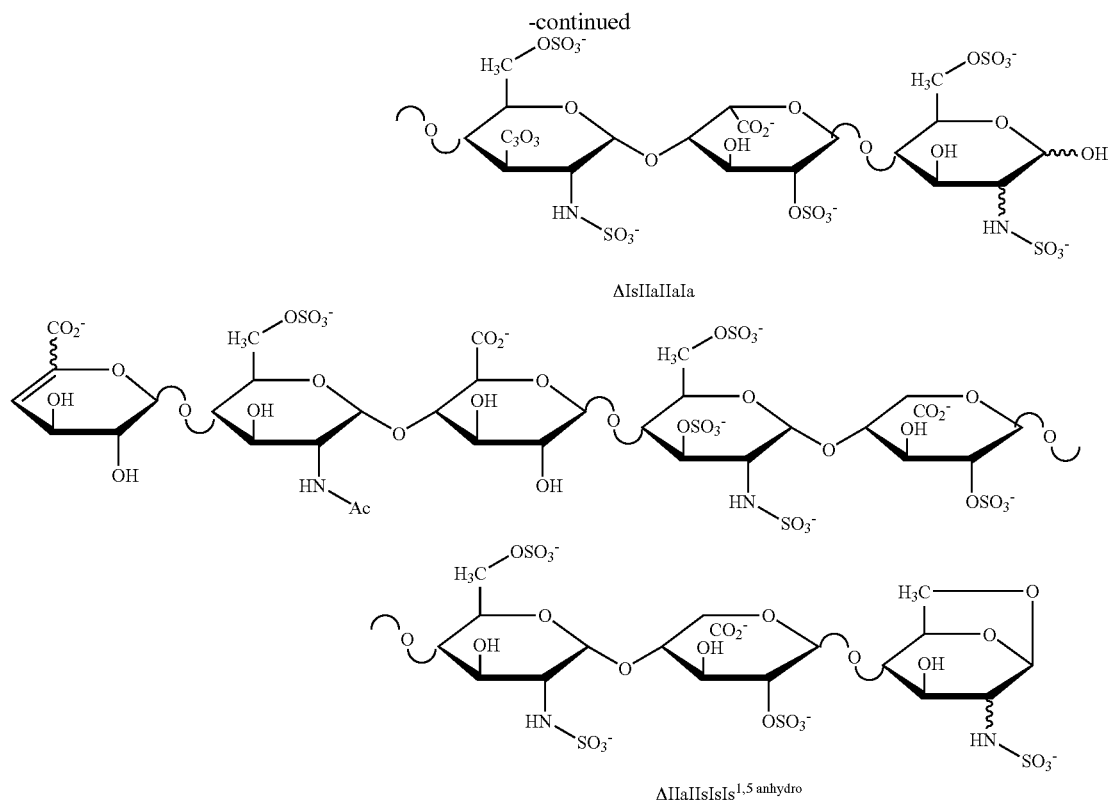

The mixture is administered subcutaneously to 3 male dogs of the beagle breed at a target dose with regard to each of these 3 constituents of 0.5 mg/kg. The administration solution is a 0.9% NaCl solution of the mixture of the 3 octasaccharides at the target concentration of 0.5 mg/ml. Blood samples of 5 ml are withdrawn at the times 0, 0.25 h, 0.5 h, 1 h, 2 h, 4 h, 6 h, 8 h, 24 h, 30 h and 48 h after administration. The blood samples withdrawn are collected in tubes containing 400 µl of a CTAD (citrate, theophylline, adenosine, dipyridamole) mixture. After homogenization, the solution is centrifuged at 3000 g at 15° C. for 15 min. The plasma supernatant is recovered and stored at −20° C. until use.

For the treatment of the plasma before HPLC injection, approximately 1 ml of plasma is withdrawn and weighed, to which 50 µl of a solution of the internal standard at a concentration of approximately 0.02 g/l are added.

The internal standard is chosen so that it is structurally as close as possible to the products to be analyzed. Its structure is given below.

The tetrasaccharide used makes it possible to correct the potentional influence of the variations in the extraction yield.

The plasma is treated and analyzed by HPLC.

The results obtained are represented in table 1. The corresponding chromatograms are represented in FIG. 1.

TABLE 1

Monitoring of the plasma concentration (µM) of the 3 octasaccharides as a function of the time after administration

| Time (hours) | | Dog 2 | Dog 3 |
|---|---|---|---|
| | $\Delta\text{IIaIIsIsIs}^{1,6\text{-}anhydro}$: concentration in µmol/l | | |
| | Dog 1 | | |
| 0 | 0.00 | 0.00 | 0.00 |
| 0.25 | 0.05 | 0.05 | 0.06 |

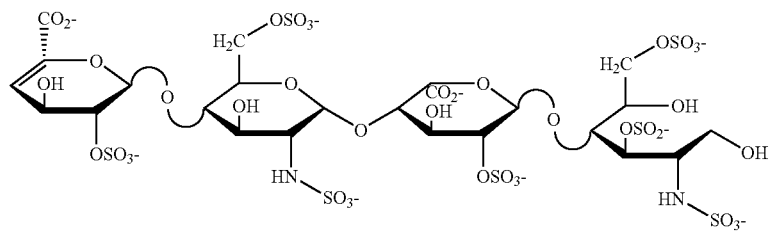

TABLE 1-continued

Monitoring of the plasma concentration (μM) of
the 3 octasaccharides as a function of the time after administration

| Time (hours) | | Dog 2 | Dog 3 |
|---|---|---|---|
| 0.5 | 0.17 | 0.10 | 0.17 |
| 1 | 0.34 | 0.21 | 0.24 |
| 2 | 0.56 | 0.32 | 0.34 |
| 4 | 0.44 | 0.30 | 0.46 |
| 6 | 0.37 | 0.37 | 0.38 |
| 8 | 0.30 | 0.25 | 0.30 |
| 24 | 0.06 | 0.05 | 0.05 |
| 30 | 0.03 | 0.03 | 0.04 |
| 48 | 0.01 | 0.01 | 0.01 |
| ΔIIaIIsIsIs: concentration in μmol/l Dog 1 | | | |
| 0 | 0.00 | 0.00 | 0.00 |
| 0.25 | 0.04 | 0.05 | 0.06 |
| 0.5 | 0.18 | 0.10 | 0.17 |
| 1 | 0.33 | 0.20 | 0.24 |
| 2 | 0.59 | 0.32 | 0.33 |
| 4 | 0.47 | 0.30 | 0.45 |
| 6 | 0.36 | 0.37 | 0.36 |
| 8 | 0.28 | 0.26 | 0.29 |
| 24 | 0.04 | 0.04 | 0.04 |
| 30 | 0.02 | 0.01 | 0.02 |
| 48 | 0.00 | 0.00 | 0.00 |
| ΔIsIIaIIsIs: concentration in μmol/l Dog 1 | | | |
| 0 | 0.00 | 0.00 | 0.00 |
| 0.25 | 0.01 | 0.03 | 0.02 |
| 0.5 | 0.07 | 0.06 | 0.09 |
| 1 | 0.16 | 0.11 | 0.13 |
| 2 | 0.33 | 0.20 | 0.19 |
| 4 | 0.27 | 0.18 | 0.28 |
| 6 | 0.22 | 0.23 | 0.23 |
| 8 | 0.18 | 0.15 | 0.19 |
| 24 | 0.04 | 0.03 | 0.03 |
| 30 | 0.02 | 0.02 | 0.02 |
| 48 | 0.00 | 0.00 | 0.00 |

Example 2

A VLMWH with an average molecular weight of 2500 Da is administered at the target dose of 1.4 mg/kg to human volunteers. Blood samples are withdrawn at the times 0, 0.25 h, 0.5 h, 0.75 h, 1 h, 1.25 h, 1.5 h, 2 h, 2.5 h, 3 h, 3.5 h, 4 h, 4.5 h, 5 h, 6 h, 7 h, 8 h, 9 h, 10 h, 12 h, 14 h and 24 h after administration.

As the VLMWH used is a complex mixture of oligosaccharides, the study was limited to certain components chosen from this mixture.

Furthermore, as an internal standard has not been found which does not interfere at the chromatographic level with one of the constituents of the mixture, assaying was carried out by taking, as molar response factor, that obtained in example 1 with regard to the affinity octasaccharides.

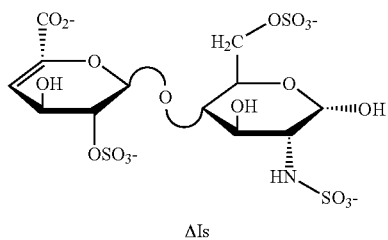

ΔIs

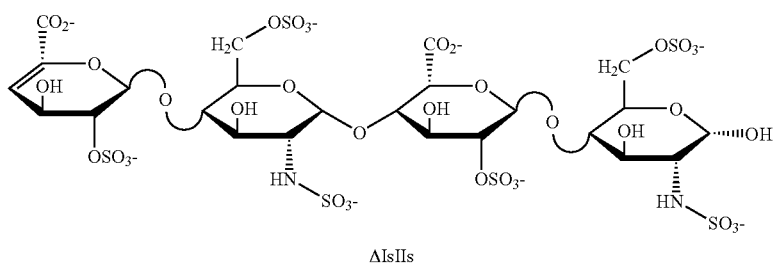

ΔIsIIs

-continued
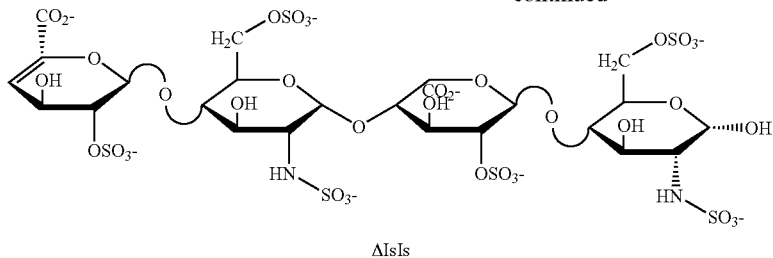
ΔIsIs
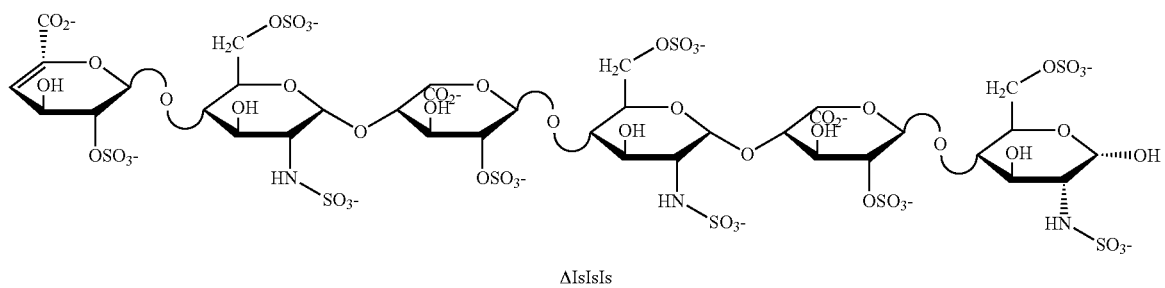
ΔIsIsIs
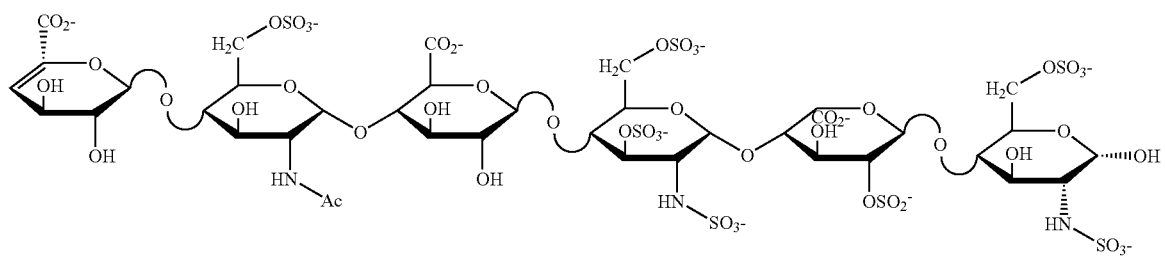
ΔIIaIsIs
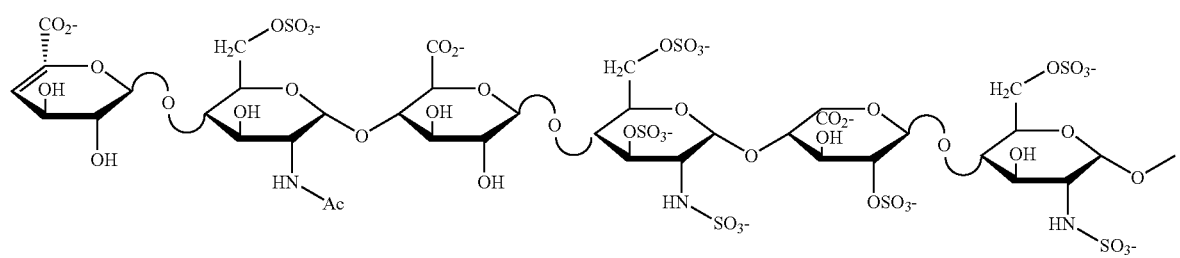
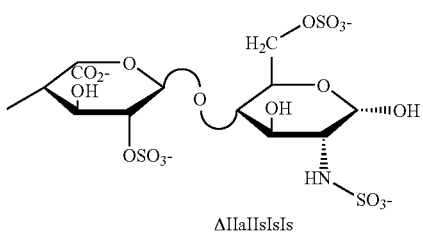
ΔIIaIIsIsIs The results demonstrate a very great difference in behavior among the oligosaccharides constituting the low molecular weight heparin studied. The oligosaccharides having an aXa activity have much slower elimination kinetics than the other sulfated oligosaccharides, which cannot be detected from monitoring aXa activity.

Figure 2:
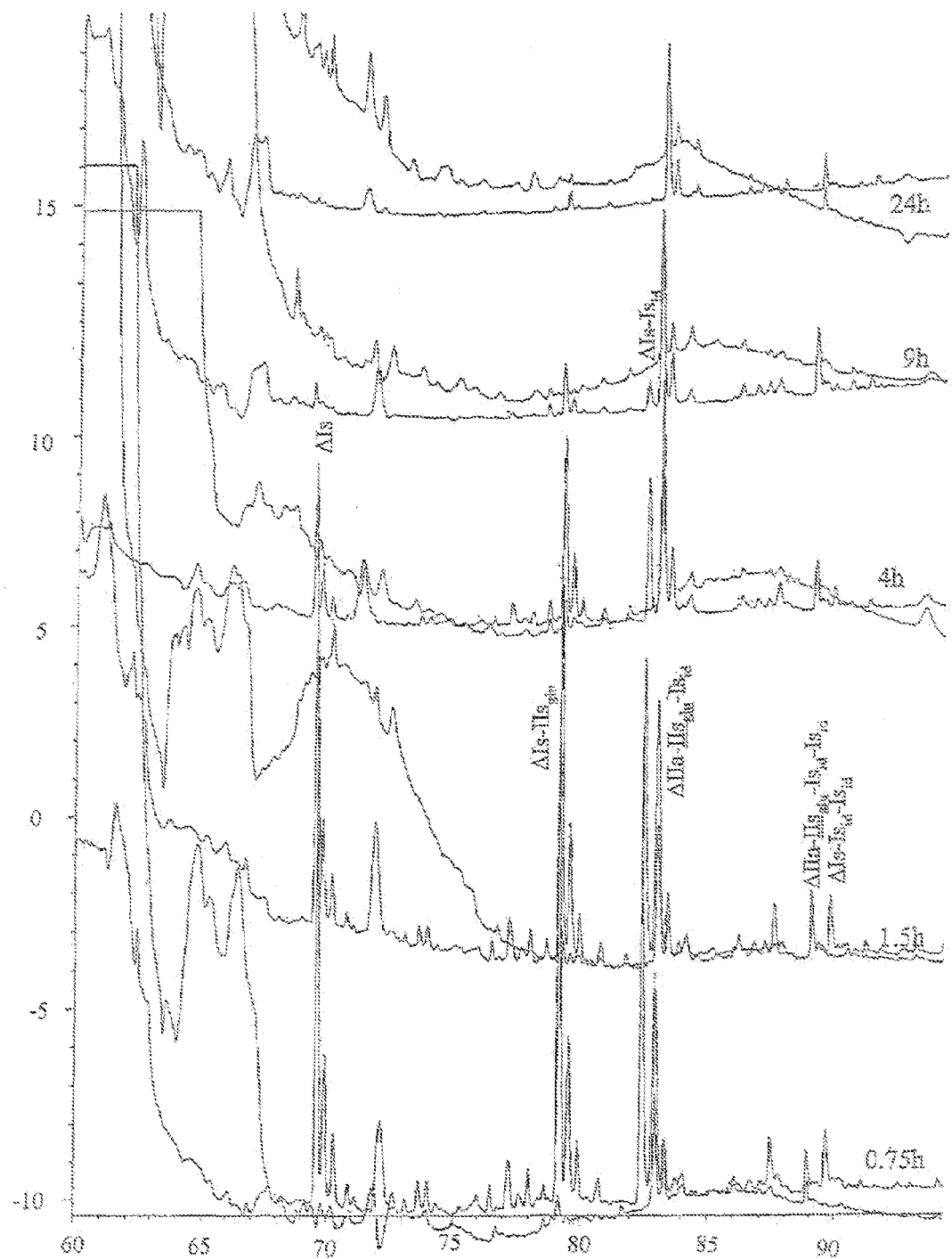
FIG. 2:
Chromatographic monitoring of the main oligosaccharides constituting a very low molecular weight heparin as a function of the time after administration.

The results obtained are represented in table 2. The corresponding chromatograms are represented in FIG. 2.

TABLE 2

Monitoring of the plasma concentration (μM) of the main oligosaccharides as a function of the time after administration

| Time in hours | ΔIs | ΔIsIIs | ΔIsIs | ΔIIaIIsIs | ΔIsIsIs | ΔIIaIIsIsIs |
|---|---|---|---|---|---|---|
| 0 | 0.00 | 0.00 | 0.00 | 0.00 | 0.00 | 0.00 |
| 0.25 | 0.24 | 0.20 | 0.16 | 0.05 | 0.02 | 0.01 |
| 0.5 | 0.30 | 0.30 | 0.24 | 0.10 | 0.04 | 0.03 |
| 0.75 | 0.26 | 0.26 | 0.21 | 0.10 | 0.03 | 0.02 |
| 1 | 0.23 | 0.26 | 0.20 | 0.10 | 0.04 | 0.03 |
| 1.25 | 0.20 | 0.23 | 0.19 | 0.12 | 0.04 | 0.04 |
| 1.5 | 0.19 | 0.22 | 0.19 | 0.11 | 0.03 | 0.04 |
| 2 | 0.16 | 0.18 | 0.15 | 0.11 | 0.03 | 0.04 |
| 2.5 | 0.11 | 0.13 | 0.10 | 0.09 | 0.02 | 0.03 |
| 3 | 0.10 | 0.10 | 0.09 | 0.08 | 0.02 | 0.03 |
| 3.5 | 0.08 | 0.10 | 0.07 | 0.09 | 0.02 | 0.04 |
| 4 | 0.07 | 0.07 | 0.07 | 0.10 | 0.01 | 0.02 |
| 4.5 | 0.06 | 0.06 | 0.06 | 0.10 | 0.01 | 0.04 |
| 5 | 0.04 | 0.05 | 0.05 | 0.09 | 0.01 | 0.03 |
| 6 | 0.03 | 0.04 | 0.04 | 0.08 | 0.01 | 0.02 |
| 7 | 0.03 | 0.03 | 0.03 | 0.10 | 0.01 | 0.04 |
| 8 | 0.02 | 0.02 | 0.02 | 0.07 | 0.00 | 0.02 |
| 9 | 0.01 | 0.01 | 0.01 | 0.07 | 0.00 | 0.02 |
| 10 | 0.01 | 0.01 | 0.01 | 0.07 | 0.00 | 0.02 |
| 12 | 0.00 | 0.00 | 0.01 | 0.08 | 0.00 | 0.03 |
| 14 | 0.00 | 0.00 | 0.00 | 0.07 | 0.00 | 0.02 |
| 24 | | | | 0.05 | | 0.01 |

What is claimed is:

1. A method for the analysis of an oligosaccharide from blood plasma, comprising:
   a. treating a sample of blood plasma by filtration to produce a concentrate and a filtrate,
   b. washing the concentrate at least once with a saline solution,
   c. filtering the washed concentrate to produce additional filtrate,
   d. combining the additional filtrate with the original filtrate to form a filtered sample, and
   e. assaying the filtered sample by high performance liquid chromatography (HPLC);
wherein molecules having a molecular weight of greater than 30 kDa are retained in the concentrate of the filtration; wherein a control oligosaccharide is added to the plasma before filtration; and wherein the oligosaccharide is a β-unsaturated oligosaccharide.

2. The method according to claim 1, wherein the saline solution is a potassium chloride solution.

3. The method according to claim 1, wherein the concentration of the saline solution after addition of the concentrate is greater than or equal to 1M.

4. The method according to claim 1, wherein the concentration of the saline solution after addition of the concentrate is greater than or equal to 2M.

5. The method according to claim 2, wherein the concentration of the saline solution after addition of the concentrate is greater than or equal to 1M.

6. The method according to claim 2, wherein the concentration of the saline solution after addition of the concentrate is greater than or equal to 2M.

7. The method according to claim 1, wherein after the concentrate is washed at least with a saline solution, it is then washed with water.

8. The method according to claim 1, wherein the chromatography is an anion-exchange chromatography.

9. The method according to claim 8, wherein the chromatography is an anion-exchange chromatography on an anion-exchange column with grafting of the quaternary ammonium via a covalent bond.

10. The method according to claim 8, wherein use is made of a mobile phase which is transparent up to 200 nm.

11. The method as defined in claim 10, wherein the mobile phase is a solution of sodium perchlorate, methanesulfonate or phosphate.

12. The method as defined in claim 11, wherein the mobile phase is a sodium perchlorate solution.

13. The method according to claim 8, further comprising selectively detecting acetylated saccharides.

14. The method according to claim 13, wherein the selectively detecting acetylated saccharides is carried out by taking, as a signal, the difference between the absorption at two wavelengths chosen in such a way that the absorptivity of the nonacetylated saccharides is cancelled out.

15. The method according to claim 13, wherein the selective detection of acetylated sugars is carried out by measuring the absorption at 202-230 nm and 234 nm.

16. The method according to claim 13, wherein the selective detection of acetylated sugars is carried out by measuring the absorption at 202-230 nm, 234 nm and 280 nm.

17. The method according to claim 1, wherein the oligosaccharide is selected from: enoxaparin, octaparin, bemiparin and tinzaparin.

18. The method according to claim 1, wherein the oligosaccharide is selected from:

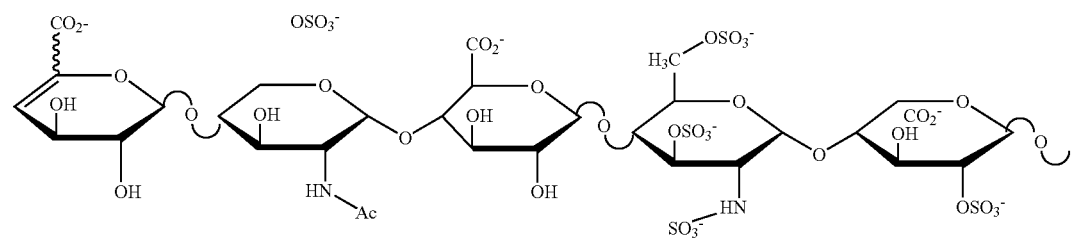

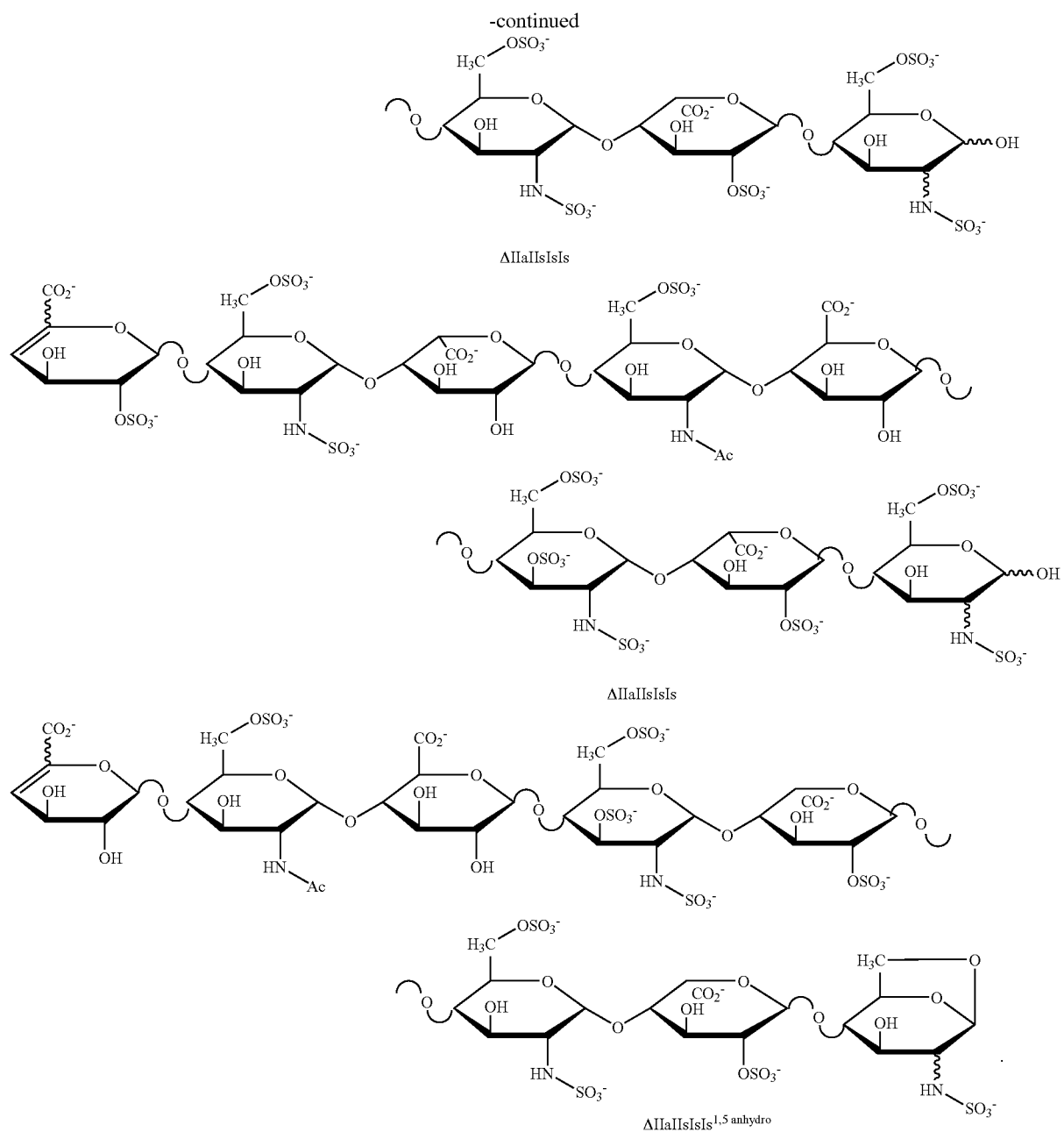
19. The method according to claim 1, wherein the oligosaccharide is selected from:
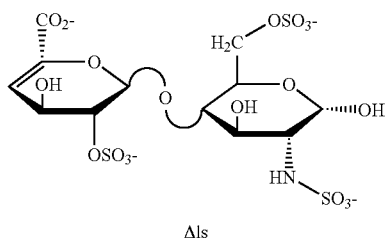

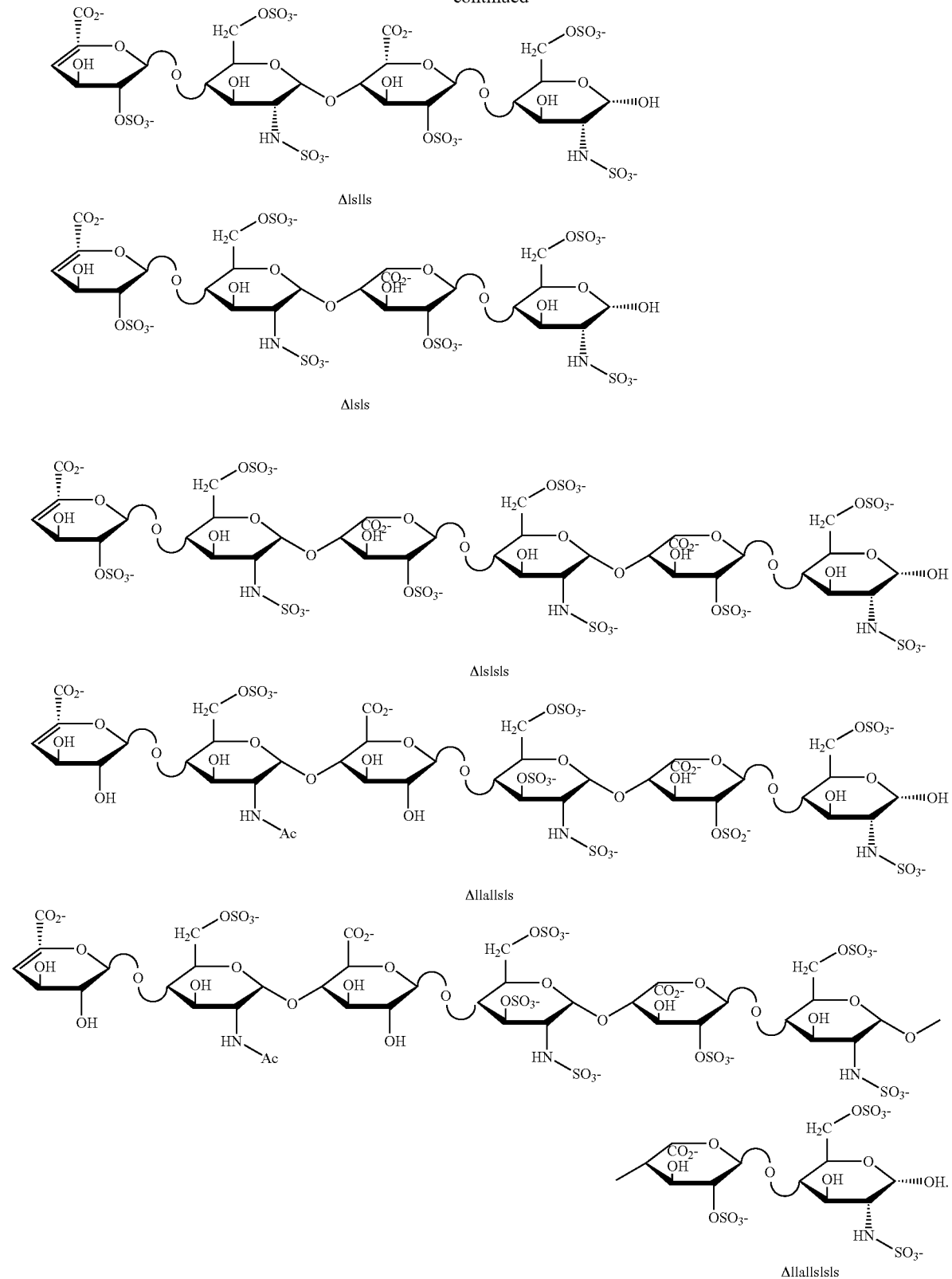

UNITED STATES PATENT AND TRADEMARK OFFICE
CERTIFICATE OF CORRECTION

PATENT NO. : 7,575,930 B2
APPLICATION NO. : 11/777431
DATED : August 18, 2009
INVENTOR(S) : Pierre Mourier et al.

It is certified that error appears in the above-identified patent and that said Letters Patent is hereby corrected as shown below:

In column 4, line 3, delete "NaClO$_4$ b $_1$N" and insert -- NaClO$_4$ 1N --, therefor.

In column 8, line 35, delete "potentional" and insert -- potential --, therefor.

In column 7-8, line 57, delete

"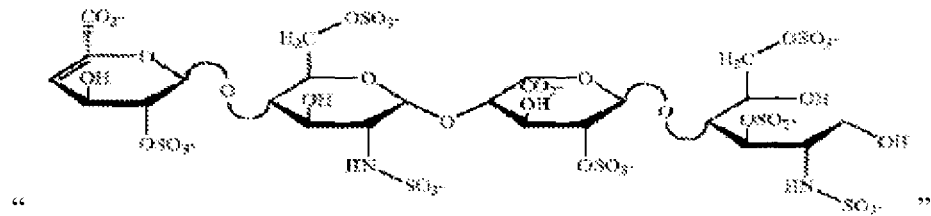"

and insert -- 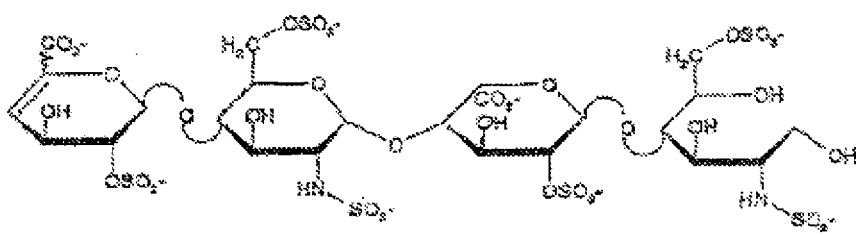 --, therefor.

Signed and Sealed this
Twenty-ninth Day of March, 2011

David J. Kappos
*Director of the United States Patent and Trademark Office*